US 11,872,040 B2

(12) United States Patent
Chatterjee et al.

(10) Patent No.: US 11,872,040 B2
(45) Date of Patent: Jan. 16, 2024

(54) METHOD AND SYSTEM FOR ASSESSMENT OF COGNITIVE LOAD FROM BIO-POTENTIALS MEASURED USING WEARABLE ENDOSOMATIC DEVICE (71) Applicant: Tata Consultancy Services Limited, Mumbai (IN)

(72) Inventors: Debatri Chatterjee, Kolkata (IN); Dibyanshu Jaiswal, Kolkata (IN); Arpan Pal, Kolkata (IN); Ramesh Kumar Ramakrishnan, Bangalore (IN); Ratna Ghosh, Kolkata (IN); Madhurima Moulick, Kolkata (IN); Rajesh Ranjan, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 476 days.

(21) Appl. No.: 17/136,899

(22) Filed: Dec. 29, 2020

(65) Prior Publication Data
US 2021/0393182 A1 Dec. 23, 2021

(30) Foreign Application Priority Data

Jun. 18, 2020 (IN) .............................. 202021025764

(51) Int. Cl.
A61B 5/16 (2006.01)
G16H 10/60 (2018.01)
(Continued)

(52) U.S. Cl.
CPC .......... *A61B 5/165* (2013.01); *A61B 5/0533* (2013.01); *A61B 5/7267* (2013.01);
(Continued)

(58) Field of Classification Search
CPC ......... A61B 5/24; A61B 2505/09; A61B 5/16; A61B 5/369; A61B 5/374; A61B 5/4484;
(Continued)

(56) References Cited

U.S. PATENT DOCUMENTS 10,722,164 B2 7/2020 Chatterjee et al.
2016/0128593 A1* 5/2016 Sinharay ................ A61B 5/165
600/544

(Continued)

FOREIGN PATENT DOCUMENTS

EP 3 498 169 A1 6/2019
WO WO 2018/042261 A1 3/2018
WO WO-2018042261 A1 * 3/2018 ........... A61B 5/0533

OTHER PUBLICATIONS

Sakar Pritam et.al. "Classification of Cognitive Load and Expertise for Adaptive Simulation Using Deep Multitask Learning", 2019 8th International Conference on Affective Computing and Intelligent Interaction (ACII), Sep. 3, 2019, pp. 496-502. DOI: 10.1109/AcII. 2019.8925507. (Year: 2019).*

(Continued)

Primary Examiner — Eric F Winakur
Assistant Examiner — Emily C Clement
(74) Attorney, Agent, or Firm — Finnegan, Henderson, Farabow, Garrett & Dunner LLP (57) ABSTRACT Direct usage of endosomatic EDA has multiple challenges for practical cognitive load assessment. Embodiments of the method and system disclosed provide a solution to the technical challenges in the art by directly using the bio-potential signals to implement endosomatic approach for assessment of cognitive load. The method utilizes a multi-channel wearable endosomatic device capable of acquiring and combining multiple bio-potentials, which are biomarkers of cognitive load experienced by a subject performing a cognitive task. Further, extracts information for classifica- (Continued)

tion of the cognitive load, from the acquired bio-signals using a set of statistical and a set of spectral features. Furthermore, utilizes a feature selection approach to identify a set of optimum features to train a Machine Learning (ML) based task classifier to classify the cognitive load experienced by a subject into high load task and low load task.

8 Claims, 7 Drawing Sheets

(51) Int. Cl.
    *G16H 50/70*     (2018.01)
    *G06N 20/00*     (2019.01)
    *A61B 5/0533*     (2021.01)
    *A61B 5/00*     (2006.01)
    *G16H 40/67*     (2018.01)

(52) U.S. Cl.
    CPC ........... *A61B 5/7278* (2013.01); *G06N 20/00* (2019.01); *G16H 10/60* (2018.01); *G16H 40/67* (2018.01); *G16H 50/70* (2018.01)

(58) Field of Classification Search
    CPC ... A61B 5/7264; A61B 5/7275; A61B 5/0006; A61B 5/4064; A61B 5/163; A61B 5/162; A61B 5/291; A61B 5/165; G16H 50/30; G16H 20/70; G06F 30/27
    See application file for complete search history.

(56) References Cited

U.S. PATENT DOCUMENTS

2019/0110726 A1     4/2019   Chatterjee et al.
2019/0175091 A1*   6/2019   Das ........................ A61B 5/165

OTHER PUBLICATIONS

Peyvand Ghaderyan et. al. "Time-Varying Singular Value Decomposition Analysis of Electrodermal Activity: A Novel Method of Cognitive Load Estimation." Elsevier, vol. 126, Oct. 2018, pp. 102-109, https://doi.org/10.1016/j.measurement.2018.05.015. (Year: 2018).*

Zangróniz et al., "Electrodermal Activity Sensor for Classification of Calm/Distress Condition", Sensors, MDPI, vol. 17, issue 10, pp. 1-14, 2017 Link: https://www.researchgate.net/publication/320359038_Electrodermal_Activity_Sensor_for_Classification_of_CalmDistress_Condition/link/59e017160f7e9bc51256cebd/download.

Kim et al., "Automatic detection of major depressive disorder using electrodermal activity", Scientific Reports, Research Gate, pp. 1-10, 2018 Link: https://www.researchgate.net/publication/329042526_Automatic_detection_of_major_depressive_disorder_using_electrodermal_activity/link/5fb56cc692851c2994e4d52c/download.

* cited by examiner

METHOD AND SYSTEM FOR ASSESSMENT OF COGNITIVE LOAD FROM BIO-POTENTIALS MEASURED USING WEARABLE ENDOSOMATIC DEVICE

PRIORITY CLAIM

This U.S. patent application claims priority under 35 U.S.C. § 119 to the Indian provisional patent application no. IN-202021025764, filed on 18 Jun. 2020. The entire contents of the aforementioned application are incorporated herein by reference.

TECHNICAL FIELD

The disclosure herein generally relates to automated assessment of cognitive load, and, more particularly, to a method and system for assessment of cognitive load from bio-potentials measured using wearable endosomatic device.

BACKGROUND

Cognitive load is the amount of mental resources required to execute a task. Psychophysiological research shows variations in the electrodermal activity of the skin with variations in cognitive load. An optimum amount of cognitive load is required for executing the task successfully, beyond which the performance of an individual degrades drastically, leading to psychological conditions like stress, anxiety etc. Thus, measuring the overall cognitive load imparted on an individual is important. Various approaches are used for assessment of cognitive load. State of the art studies mostly use exosomatic approach like Galvanic Skin Resistance (GSR) for measuring electrodermal activity (EDA) and assess cognitive load experienced by a subject. Subjective measurement includes questionnaires like NASA-TLX, SWAT etc., whereas performance based measures like task completion time, error rate etc., are also used. Research is being conducted for using various physiological parameters like heart rate, brain signals, skin conductance level, and breathing signals as markers of the cognitive load. However, continuous monitoring of cognitive load in daily life scenarios is still in an exploratory stage and requires a low cost wearable device for ease of use. Recent studies show the possibility of detecting the cognitive load from a variety of wearable sensors. One of the works in literature uses a smart watch for recording cardiac signal and extracted respiratory signal from it, which in turn is used for assessing cognitive load, while another existing work uses a combination of sensors like galvanic skin conductance (GSR) and Heart rate (HR) etc., being used for measuring mental workload in one scenario. Most of the available wearable devices either employ a GSR sensor (measuring the variations in skin conductance) or a photoplethysmogram (PPG) sensor or a combination of both.

Electrodermal activity is defined as the variation of electrical characteristics of the skin, which is typically governed by the sweat gland activity. Sweat secretion, usually driven by autonomic nervous system, causes the variation in the electrical property of the skin. Two alternative approaches used for measuring electrodermal activity are exosomatic measurements and endosomatic measurements. In the exosomatic approach, AC/DC current is passed through two electrodes placed on the skin that results in measurable changes in skin conductance level. In contrast, the endosomatic method measures the bio-potential of the skin without application of any electrical stimulus.

Endosomatic approach, which is related to both sympathetic and parasympathetic nervous system, is considered to be more reliable and physiological, compared to the exosomatic approach. Besides, the signal level in exosomatic measurements is dependent on the skin conductance level and hence, people with dry or calloused hands have significantly lower GSR value. In spite of these limitations, exosomatic approach has been used extensively to measure cognition effect as there are a number of wearable devices available in the market for exosomatic measurements. However, using endosomatic EDA has multiple challenges for practical usage of cognitive load assessment. Thus, very few prior works refer to possibility of usage of Endosomatic EDA for cognitive load detection/classification, instead prefer the exosomatic approach stating multiple challenges in using the endosomatic EDA approach. It can be noted that for the endosomatic EDA approach randomly picking bio-potential signals (bio-signals) from any part of body does not suffice to obtain accurate task classification results. Further bio-signals being of very low amplitude require specific preprocessing. Furthermore, to assess cognitive load from bio-signals into high load and low load requires right combination of features to be selected from the bio-signal, which can be then used to train a classifier for cognitive load with required accuracy. Thus, hardly any attempts have been made to address the technical challenges in using endosomatic EDA.

SUMMARY

Embodiments of the present disclosure present technological improvements as solutions to one or more of the above-mentioned technical problems recognized by the inventors in conventional systems. For example, in one embodiment, a method for assessment of cognitive load from bio-potentials measured using a wearable endosomatic device is provided.

The method comprising acquiring via a multichannel wearable endosomatic device, a plurality of bio-potential signals providing a task specific data of a subject performing a cognitive task, wherein the plurality of bio-potential signals are time stamped.

Further comprising extracting a baseline data and a task data based on time stamps associated with each of the plurality of bio-potential signals, by the one or more hardware processors, wherein the baseline data corresponds to segment of each of the plurality of bio-potential signals when the subject experiences a nil cognitive load and the task data corresponds to segment of each of the plurality of bio-potential signals when the subject experiences an active cognitive load during the cognitive task being performed.

Furthermore comprising deriving a plurality of deviation signals from the plurality bio-potential signals by: computing mean of each of the plurality of bio-potential signals comprising the base-line data and the task data; and subtracting each of the base-line data and the task data from the corresponding plurality of bio-potential signals.

Thereafter, extracting a plurality of features from the plurality of deviation signals, wherein the plurality of features comprising a statistical set of features and a spectral set of features and determining an optimum set of features from the plurality of features using a Feature Discovery Platform (FDP), wherein the FDP selects the optimum feature set in accordance with the cognitive task.

Furthermore, training a classifier for classifying the cognitive task into one of a high load task and a low load task using the optimum set of features and utilizing the trained classifier to classify the cognitive task performed by the subject in real time into the high load task and the low load task.

In another aspect, a system for assessment of cognitive load from bio-potentials measured using a wearable endosomatic device, the system comprising: a memory storing instructions; one or more Input/Output (I/O) interfaces; and one or more hardware processors coupled to the memory via the one or more I/O interfaces, wherein the one or more hardware processors are configured by the instructions for: acquiring via a multichannel wearable endosomatic device, a plurality of bio-potential signals providing a task specific data of a subject performing a cognitive task, wherein the plurality of bio-potential signals are time stamped.

Further extracting a baseline data and a task data based on time stamps associated with each of the plurality of bio-potential signals, by the one or more hardware processors, wherein the baseline data corresponds to segment of each of the plurality of bio-potential signals when the subject experiences a nil cognitive load and the task data corresponds to segment of each of the plurality of bio-potential signals when the subject experiences an active cognitive load during the cognitive task being performed.

Furthermore deriving a plurality of deviation signals from the plurality bio-potential signals by: computing mean of each of the plurality of bio-potential signals comprising the base-line data and the task data; and subtracting each of the base-line data and the task data from the corresponding plurality of bio-potential signals.

Thereafter, extracting a plurality of features from the plurality of deviation signals, wherein the plurality of features comprising a statistical set of features and a spectral set of features and determining an optimum set of features from the plurality of features using a Feature Discovery Platform (FDP), wherein the FDP selects the optimum feature set in accordance with the cognitive task.

Furthermore, training a classifier for classifying the cognitive task into one of a high load task and a low load task using the optimum set of features and utilizing the trained classifier to classify the cognitive task performed by the subject in real time into the high load task and the low load task.

In yet another aspect, there are provided one or more non-transitory machine-readable information storage mediums comprising one or more instructions, which when executed by one or more hardware processors causes a method for assessment of cognitive load from bio-potentials measured using a wearable endosomatic device. The method comprises acquiring via a multichannel wearable endosomatic device, a plurality of bio-potential signals providing a task specific data of a subject performing a cognitive task, wherein the plurality of bio-potential signals are time stamped.

Further comprising extracting a baseline data and a task data based on time stamps associated with each of the plurality of bio-potential signals, by the one or more hardware processors, wherein the baseline data corresponds to segment of each of the plurality of bio-potential signals when the subject experiences a nil cognitive load and the task data corresponds to segment of each of the plurality of bio-potential signals when the subject experiences an active cognitive load during the cognitive task being performed.

Furthermore comprising deriving a plurality of deviation signals from the plurality bio-potential signals by: computing mean of each of the plurality of bio-potential signals comprising the base-line data and the task data; and subtracting each of the base-line data and the task data from the corresponding plurality of bio-potential signals.

Thereafter, extracting a plurality of features from the plurality of deviation signals, wherein the plurality of features comprising a statistical set of features and a spectral set of features and determining an optimum set of features from the plurality of features using a Feature Discovery Platform (FDP), wherein the FDP selects the optimum feature set in accordance with the cognitive task.

Furthermore, training a classifier for classifying the cognitive task into one of a high load task and a low load task using the optimum set of features and utilizing the trained classifier to classify the cognitive task performed by the subject in real time into the high load task and the low load task.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following embodiments described herein, with the true scope being indicated by the following claims.

Embodiments herein provide a method and system for assessment of cognitive load from bio-potentials measured using wearable endosomatic device. The method disclosed provides a solution to the technical challenges in the art while directly using the bio-potential signals (interchangeably referred as bio-signals) to implement endosomatic approach by:

1) Utilizing a multichannel wearable endosomatic device capable of acquiring and combining multiple bio-potentials, which are biomarkers of cognitive load experienced by a subject performing a cognitive task. The multiple bio-potentials are associated with appropriately chosen multiple body parts. Bio-potentials, alternatively referred as skin potentials, when measured at different body locations might not give a good biomarker of cognitive load, however, when combined together, they serve as a reliable biomarker. The multichannel wearable device used is a device referred in one of the patent application No. 201931038304 filed at IPO, which provides an expert system to determine the human condition using bilateral endosomatic EDA and the method thereof. The device referred in the patent application No. 201931038304 is a multi-channel endosomatic EDA device capable of capturing bio-potential signal directly form a subject. However, the patent application No. 201931038304 limits to design of the EDA device and does not focus on detailed approach of usage of captured bio-potential signals for cognitive load assessment, which is provided by the method disclosed herein. The details of the multi-channel endosomatic EDA device are not explained herein for brevity.

2) Extracting information required, for classification of the cognitive load, from the acquired bio-signals using a set of statistical and a set of spectral features.

3) Utilizing a feature selection approach to identify a set of optimum features to train a Machine Learning (ML) based task classifier to classify the cognitive load experienced by a subject into high load task and low load task.

4) Further, in an embodiment the method disclosed combines bio-potentials acquired from GSR and bio-potential features via the wearable endosomatic device for increasing overall classification accuracy.

Referring now to the drawings, and more particularly to FIG. 1 through FIG. 5B, where similar reference characters denote corresponding features consistently throughout the figures, there are shown preferred embodiments and these embodiments are described in the context of the following exemplary system and/or method.

Figure 1:
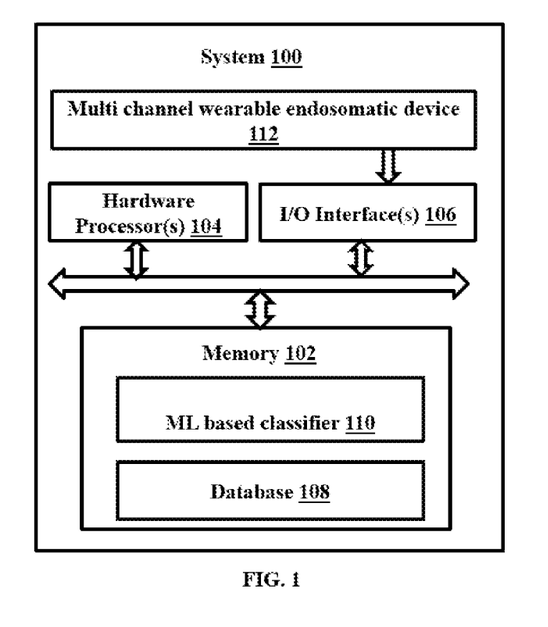
FIG. 1 illustrates a system for assessment of cognitive load from bio-potentials measured using a wearable endosomatic device, according to some embodiments of the present disclosure.

FIG. 1 illustrates a system for assessment of cognitive load from bio-potentials measured using a wearable endosomatic device, according to some embodiments of the present disclosure.

In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The database 108 may store information but is not limited the acquired bio-potentials using a multichannel endosomatic wearable device 112, the set of statistical features and the set of spectral features extracted from the bio-potentials. Further, the database 108 stores information pertaining to inputs fed to the system 100 and/or outputs generated by the system (e.g. at each stage), specific to the methodology described herein. Specifically, the database 108 stores information being processed at each step of the proposed methodology. The memory 102 includes multiple modules (not shown) such as an optimum feature selection module like a Feature discovery platform (FDP). Also, the memory 102 includes a ML based classifier 110 that is trained using the features acquired bio-potential signals by utilizing the optimum features of the bio-signals. The trained ML based classifier 110 can then be used in real time scenarios to classify the cognitive load experienced buy a subject under observation and wearing a multichannel endosomatic device 112. As explained above, the multichannel endosomatic device is capable of capturing bio-potential signal directly from a subject and provide calibrated bio-potential signals with both static calibration and dynamic calibration. However, the patent application No. 201931038304 limits to design of the EDA device and does not focus on detailed approach of usage of captured bio-potential signals for cognitive load assessment, which is provided by the method disclosed herein. The details of the multi-channel endosomatic EDA device, which is typically a four channel device are not explained in detail herein for brevity, however explained in brief in the experimental set up described below.

Figure 2A:
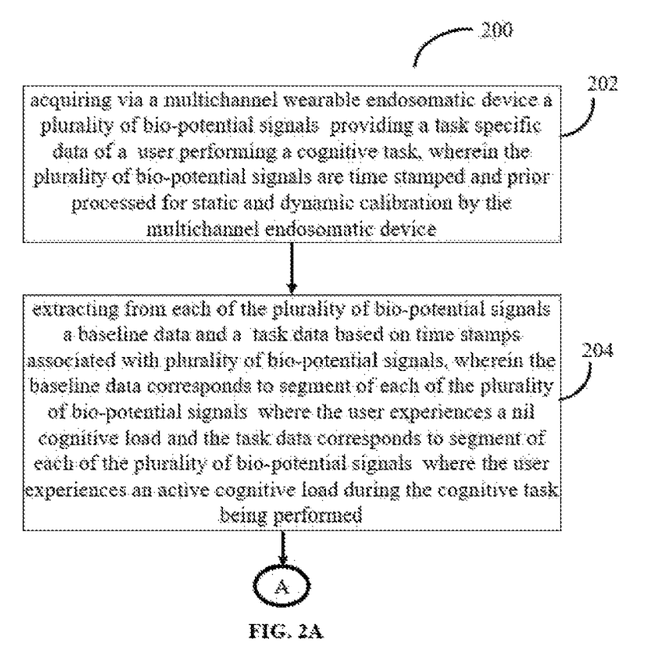
FIG. 2 is a flowchart illustrating a method for assessment of cognitive load from bio-potentials measured using wearable endosomatic device, according to some embodiments of the present disclosure.
Figure 2B:
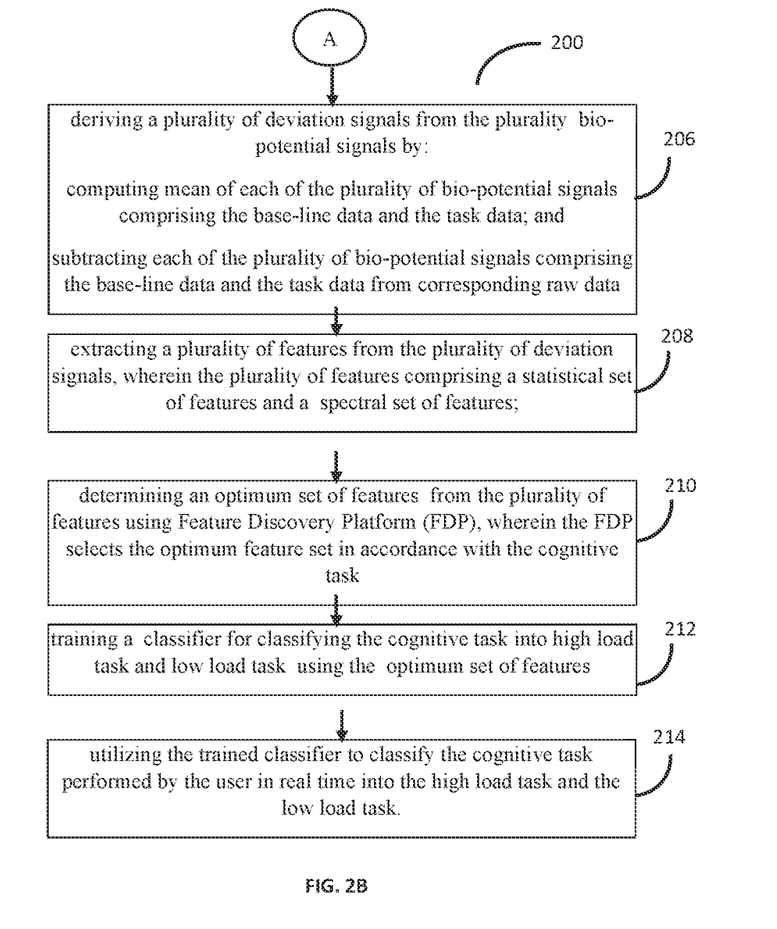
Figure 3:
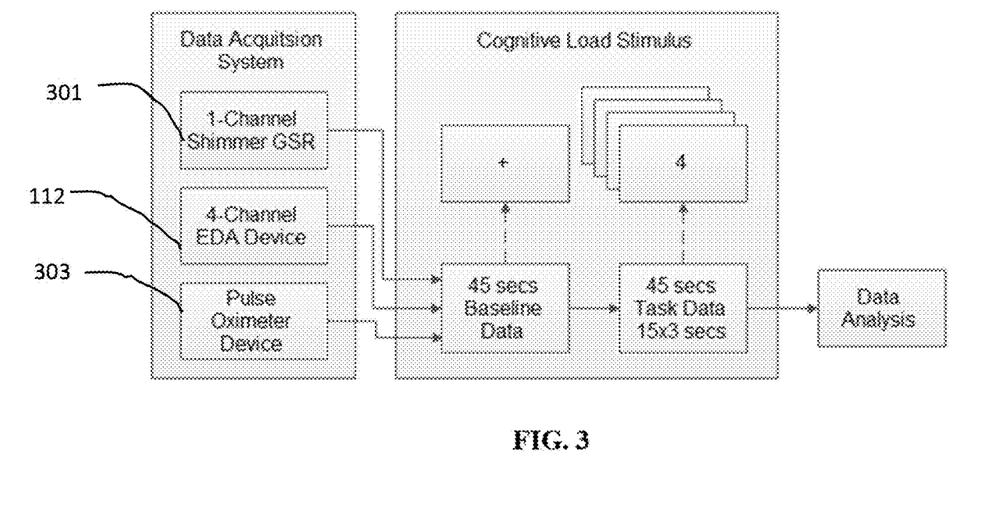
FIG. 3 is an architectural overview of the system of FIG. 1, according to some embodiments of the present disclosure.
Figure 4:
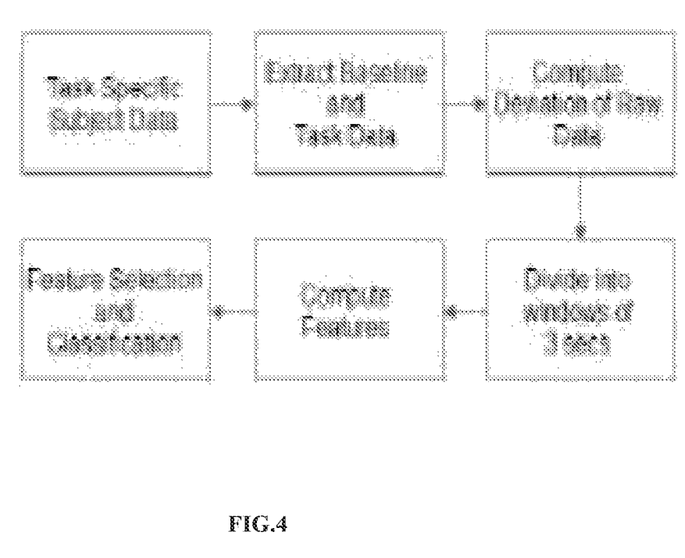
FIG. 4 illustrates functional block diagram of the system of FIG. 1, according to some embodiments of the present disclosure.

Functions of the components of system 100 are explained in conjunction with flow diagrams depicted in FIG. 2, and architectural and functional block diagrams of system 100 as depicted in FIG. 3 and FIG. 4.

FIG. 2 is a flowchart illustrating a method for assessment of cognitive load from bio-potentials measured using wearable endosomatic device, according to some embodiments of the present disclosure.

In an embodiment, the system 100 comprises one or more data storage devices or the memory 102 operatively coupled to the processor(s) 104 and is configured to store instructions for execution of steps of the method depicted in FIGS. 2 through 4 by the processor(s) or one or more hardware processors 104. The steps of the method of the present disclosure will now be explained with reference to the components or blocks of the system 100 as depicted in FIG. 1 and the steps of flow diagram as depicted in FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously. The method 200 is further explained in conjunction with FIGS. 3 and 4 supported with experimental results.

Referring to the steps of the method 200 in FIG. 2, at step 202, the one or more hardware processors 104 are configured to acquire via the multichannel wearable endosomatic device 112 a plurality of bio-potential signals providing a task specific data of a user or subject performing a cognitive task, wherein the plurality of acquired bio-signals are time stamped. Furthermore, the acquired bio-potential signal are priori processed by the multichannel bio-potential device for static calibration and dynamic calibration and provide calibrated bio-potentials for further processing.

At step 204, the one or more hardware processors 104 are configured to extract from each of the plurality of bio-potential signals a baseline data and a task data based on time stamps associated with plurality of bio-potential signals. The baseline data corresponds to segment of each of the plurality of bio-potential signals when the user experiences a nil cognitive load and the task data corresponds to segment of each of the plurality of bio-potential signals when the user experiences an active cognitive load during the cognitive task being performed;

At step 206, the one or more hardware processors 104 are configured to derive a plurality of deviation signals from the plurality bio-potential signals by: a) computing mean of each of the plurality of bio-potential signals comprising the base-line data and the task data; and b) subtracting the base-line data and the task data from corresponding acquired bio-potential signals, alternatively referred as raw data.

At step 210, the one or more hardware processors 104 are configured to extract a plurality of features from the plurality of deviation signals, wherein the plurality of features comprising a statistical set of features and a spectral set of features. The set of statistical features comprises computing by using the task data mean, median, standard deviation, skewness, kurtosis, minimum and maximum levels of the plurality of bio-potential signals. Also computed is normalized kurtosis and normalized variance values with respect to the baseline data and the task data. The set of spectral features comprises total power, mean power, mean frequency, power at mean frequency, median frequency, power at median frequency, peak frequency, peak power, signal band-power, first moment, second moment and third moment. Thus, a total of 21 features per channel, with a four channel device takes the total features to 21*4=84.

At step 212, the one or more hardware processors 104 are configured to determine an optimum set of features from the plurality of features using Feature Discovery Platform (FDP), wherein the FDP selects the optimum feature set in accordance with the cognitive task.

At step 214, the one or more hardware processors 104 are configured to train the classifier (ML based classifier) 112 for classifying the cognitive task into high load task and low load task using the optimum set of features.

At step 216, the one or more hardware processors 104 are configured to utilize the trained classifier to classify the cognitive task performed by the user in real time into the high load task and the low load task.

FIG. 3 is an architectural overview of the system of FIG. 1, according to some embodiments of the present disclosure.

Data acquisition and analysis: The method disclosed herein identifies the bio-markers of mental workload (cognitive load) from bio-potentials measured using endosomatic EDA, alternatively referred simply as EDA. As depicted in in FIG. 3 a four channel wearable endosomatic device (the multichannel wearable endosomatic device 112) records the bio-potentials from fingers of both hands and both legs of a subject while performing the task. Typically, the bandwidth of the EDA signal lies in the range 0-3 Hz, thus the sampling frequency of the wearable endosomatic device 112 was set to 20 samples/seconds. Additionally, a Shimmer™ GSR device 301 is used for recording skin conductance response in order to correlate the findings obtained from EDA response with that of GSR. The sampling frequency of the Shimmer™ GSR device 301 is set to 51.2 Hz. Also used a finger wearable pulse oximeter 303 to check that pulse rate of the participants (subjects) were well within the normal range (60-140 BPM) throughout the experiment. Bio-potentials recorded during execution of tasks from hands and feet are directly acquired into the system/data acquisition system 100 without applying any filters. Systematic static calibration and dynamic calibration of the bio-potential acquisition system is performed.

The overall approach adopted for processing sensor data is depicted with a functional block diagram of the system 100 of FIG. 1, according to some embodiments of the present disclosure. Recorded sensor data (acquired bio-potentials signals) are first divided into the task data and the baseline data based on timestamps. These data are then processed to derive features. Finally, optimum feature set selection technique such as the feature discovery platform is used to select an optimum set of features, which are then fed to a classifier (ML based classifier 112) for classification of low and high cognitive loads. The acquired bio-potential signals are analyzed in terms of deviation signal of the measured bio-potentials. For deriving the deviation signals, the mean of the whole signal (baseline+task) is computed and then subtracted from the data acquired during the task. The deviation signals under rest condition typically lie within +/−20 mV range, as reported in one of the prior works. However, the method disclosed herein identifies that during task interval, 99% of the EDA deviation signals lie within +/−10 mV range. The deviation signals obtained from the recorded left and right hand bio-potentials are then identified as LH and RH signals respectively. Similarly, those obtained from left and right leg bio-potentials are identified as LL and RL signals respectively. From these signals, some statistical features like mean, median, standard deviation, skewness, kurtosis, minimum and maximum levels. For analyzing the individual responses to mental workload, two new features are used, which are termed as normalized kurtosis and normalized variance respectively that measure of change in power distribution w.r.t baseline. These normalized kurtosis and variance values obtained during each task window with respect to the subject specific baseline values of the respective features. Hence, in total 9 statistical features are computed. In addition, the frequency distribution of these deviation signals are also analyzed, by using tools such as MATLAB's™ "pwelch" function for estimating the power spectral density of the signals. Spectral features considered include total power, mean power, mean frequency, power at mean frequency, median frequency, power at median frequency, peak frequency, peak power, signal band-power, first moment, second moment and third moment. Hence, the feature vector consisted of total 21 features (9 statistical and 12 spectral). Four such feature vectors were obtained for 4 different EDA channels (LH, RH, LL, RL). The raw GSR data, collected using Shimmer™ GSR device 301, is passed through a Finite Impulse Response (FIR) filter having passband between 0-4 Hz, since most of the skin conductance response lies within that range. The same 21 features (9 statistical and 12 spectral features) are also computed from filtered GSR data also. The EDA and GSR features obtained during execution of low load and high load tasks have been classified using a number of classifiers. However, random forest was found to outperform all. Both EDA and GSR task data were subdivided into a number of windows and all features were calculated on these windowed data. For estimating the performance of the classifier, 10 fold cross-validation was performed. The classification accuracy is calculated using GSR features as well as using endosomatic EDA features only.

Once the plurality of features as extracted, the method disclosed comprises selecting the most significant features using the state of art FDP, which is an automated framework, used to perform time-series analytics. In case of classification task, the FDP extracts signal property based generic features (SPGF) and provides a recommended set of features and learn by exploiting novel relax greedy search approach that efficiently searches over ranked feature space. Recommended features along with learned model (classifier with tuned hyper parameters) are used to derive the inference in the test data. This platform enables fusing any domain specific features along with SPGF and does the recommendation of features on the augmented feature space. In addition to this, the method disclosed also uses maximal information coefficient (MIC) based approach for feature selection for comparative study.

Experiment design and data collection: A mental addition task explained in prior work 'Estimation of cognitive load based on the pupil size dilation' is used for imparting low and high cognitive load. A set of numbers were presented to the participants one after another. Participants were instructed to add these numbers mentally and report at the end of the session. Each number was shown on the screen for a duration of 3 seconds. In a particular session, 15 such numbers were shown one after another. Single digit numbers (1, 2, 3 and 5) were used for low cognitive load session and double digit numbers (7 through 19 except 10 and 15) were used to impart high cognitive load. 24 healthy university students (14 male, 10 female, mean age: 25+/−4 years) volunteered for the study. Ethical clearance was obtained from a relevant committee of the university. The population is selected based on an understanding that students are best fit for studies involving cognitive load. A written consent was taken from all the participants before data collection. All the participants appeared for both low and high load tasks. For half of the participants, the low load task was administered first followed by high load task. Reverse order was followed for remaining participants.

The numbers were shown on the LCD screen placed at a distance of approximately 60 cm from the participant. During execution of the task, skin bio-potentials were recorded using the multichannel endosomatic device 112. This is a 4-channel device (multichannel wearable endosomatic device 112) and hence we collected skin potentials from both hands (left and right) and leg (left and right). The sensors are connected to legs. The electrodes were attached to the middle phalanges of middle and index fingers of the hands and of second and middle toes of the legs. Shimmer device was connected in lower phalanges of index and middle finger of the left hand. At the beginning of each session, a black cross was shown on the white screen for 45 seconds. Participants were asked to concentrate on the cross and this period was treated as baseline period. After this, either low or high load task (45 seconds) was administered. Once a task session (low load or high load) is over, 10 minutes rest period was given, during which the participants were instructed to relax. After that, the second task was administered.

Figure 5A:
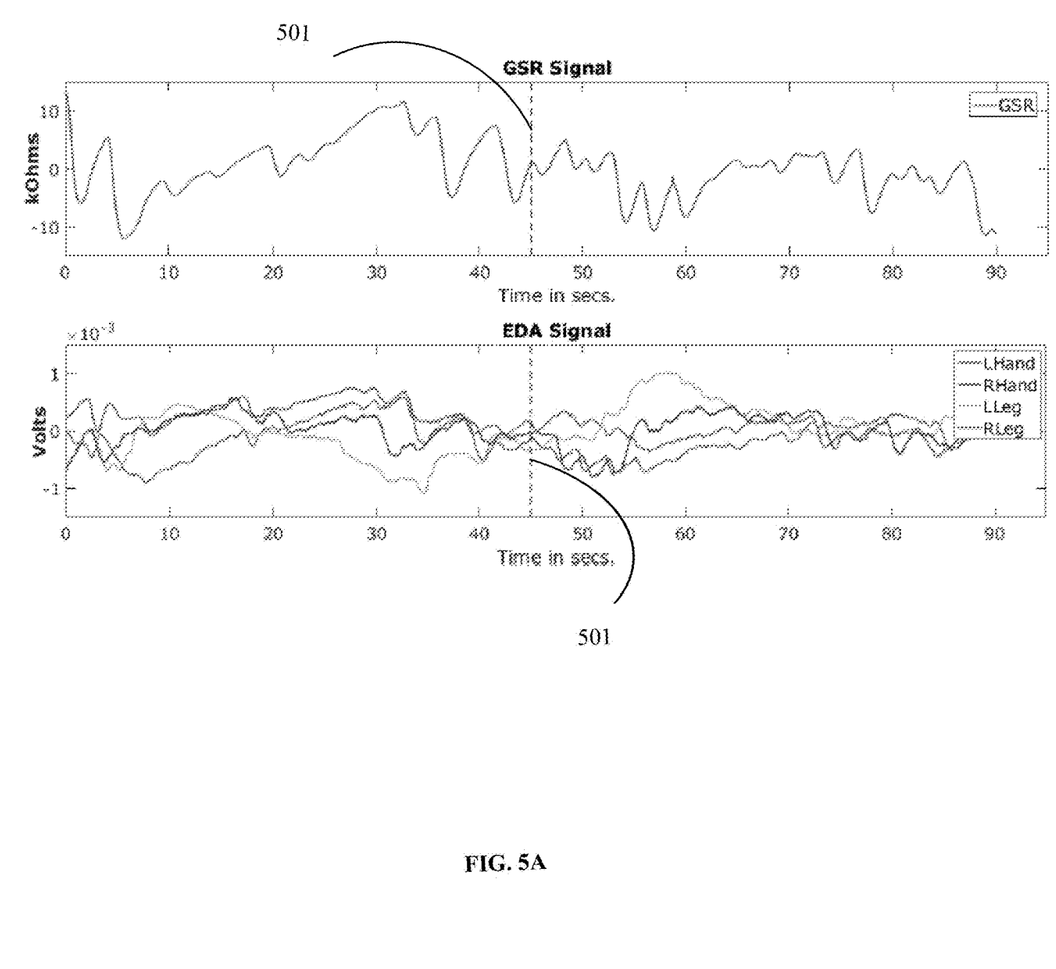
FIG. 5A and FIG. 5B depict Galvanic Skin Conductance (GSR) deviation signals and endosomatic electrodermal activity (EDA) deviation signals for low load task and high load cognitive tasks respectively, according to some embodiments of the present disclosure.
Figure 5B:
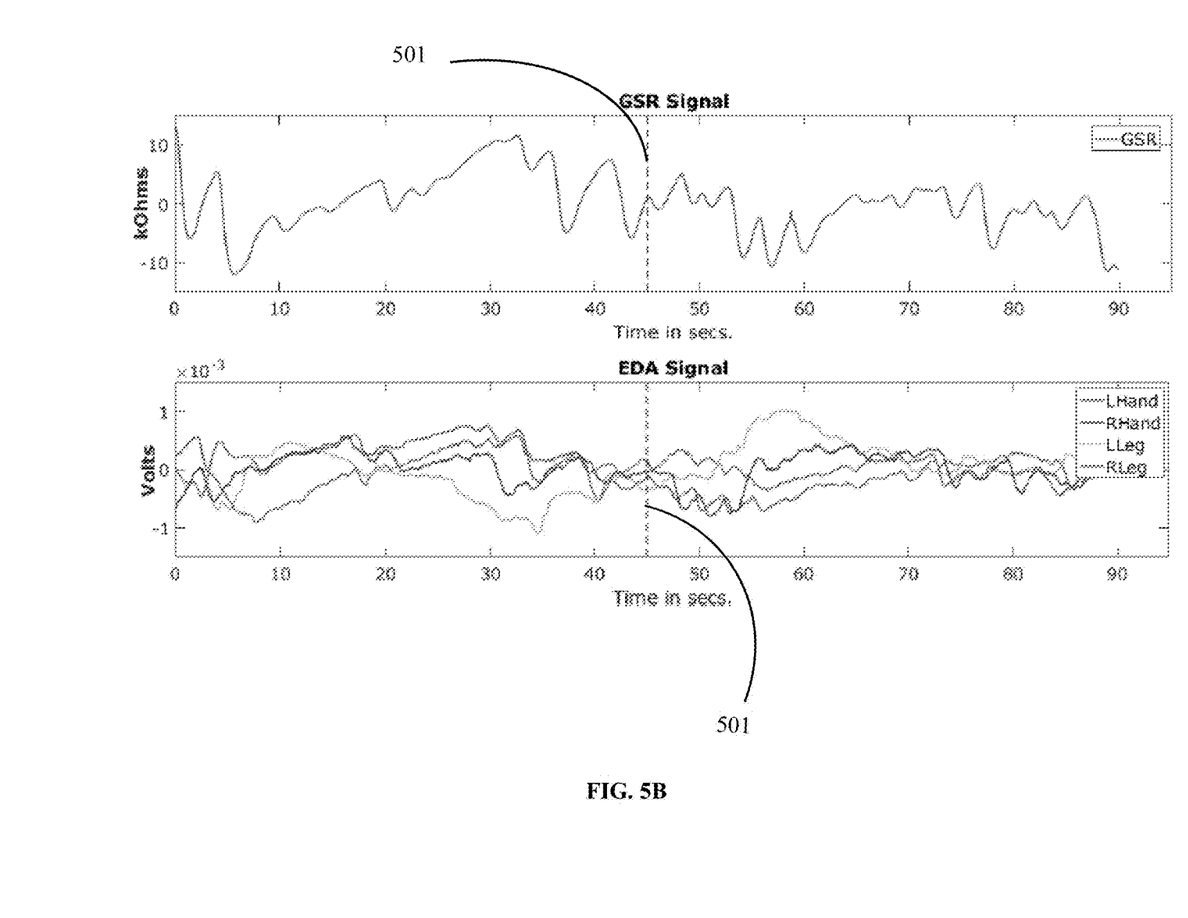

EXPERIMENTAL SET UP AND RESULTS: FIG. 5A and FIG. 5B depict Galvanic Skin Conductance (GSR) deviation signals and endosomatic electrodermal activity (EDA) deviation signals for low load task and high load cognitive tasks respectively, according to some embodiments of the present disclosure. FIGS. 5A and 5B show the deviation GSR data and EDA deviation signals for all 4-channels for a particular participant (subject) for low and high load tasks respectively. The vertical dotted line (501) in the plot indicates start time of the low/high load task. Hence, left side of this line represents the baseline signal and right side indicates the signals acquired during task interval. It is observed that all 4 deviation signals mostly correlate with the GSR signals, although with some variable lag (usually GSR lags EDA signal by few seconds). We have also observed that across participants maximum deviation is obtained in the leg signals (both RL and LL) and also, there are visible differences between EDA signals recorded for low and high load tasks. Literature suggest that there are differences in electrodermal activities recorded from left and right hand. Prior works have shown significant difference in left and right EDA (exosomatic) during long term daily wear for assessing stress. Also analyzed is if this bilateral asymmetry is observable in the deviation signals for various levels of cognitive load. Significant differences were not observed between left and right deviation signals for low and high cognitive loads. Shimmer™ GSR device 301 is an active device which sends a very small amount of current for measuring the skin conductance level. On the other hand, endosomatic EDA is a uses a passive device (multichannel wearable endosomatic device 112). It was observed that the EDA bio-potentials get affected to some extent if both Shimmer and EDA device are connected together. However, results show that it is still possible to find reliable biomarkers of cognitive load from EDA data. This characteristics was observed for all the participants (subjects). Table 1 shows the average classification performance obtained for GSR and proposed approach using various classifiers.

TABLE 1

Comparison of Average classification metrics using GSR and Proposed system

| Classifier | | GSR | Proposed System | | | | |
| --- | --- | --- | --- | --- | --- | --- | --- |
| | | | LH | RH | LL | RL | All |
| SVM | f-score | 0.57 | 0.54 | 0.56 | 0.64 | 0.60 | 0.69 |
| | Sensitivity | 0.58 | 0.54 | 0.54 | 0.65 | 0.63 | 0.96 |
| | Specificity | 0.57 | 0.57 | 0.62 | 0.63 | 0.54 | 0.19 |

TABLE 1-continued

Comparison of Average classification
metrics using GSR and Proposed system

| Classifier | | GSR | Proposed System | | | | |
|---|---|---|---|---|---|---|---|
| | | | LH | RH | LL | RL | All |
| Random forest | f-score | 0.71 | 0.60 | 0.64 | 0.72 | 0.69 | 0.83 |
| | Sensitivity | 0.70 | 0.60 | 0.63 | 0.69 | 0.72 | 0.85 |
| | Specificity | 0.72 | 0.61 | 0.68 | 0.76 | 0.64 | 0.81 |
| KNN | f-score | 0.56 | 0.52 | 0.64 | 0.63 | 0.55 | 0.71 |
| | Sensitivity | 0.56 | 0.52 | 0.63 | 0.62 | 0.55 | 0.71 |
| | Specificity | 0.58 | 0.53 | 0.66 | 0.64 | 0.56 | 0.71 |

A support vector machine (SVM) is used random forest and KNN classifiers. Both GSR (21 features) and proposed EDA features (all 84 features) were calculated over windows of duration 3 seconds. The window duration was chosen to be 3 seconds as since presented or displayed a number to the participants under test in every 3 seconds. The results are generated using 10 fold cross validation. We have used classification algorithms of MATLAB™ for generating Table 1. It is observed that for both GSR and EDA signals, random forest classifier is the best situated one. Also observed is that the average accuracy for hand channels (LH and RH) are less compared to that obtained for legs (LL and RL). It is to be observed that maximum f-score value obtained is 0.83, which corresponds to an accuracy of 83%, when we consider all 4 available EDA channels in union. For GSR, best performance is obtained with random forest classifier with a f-score of 0.71 and corresponding accuracy of 71.5%. Next, an optimum set of features was derived from the from EDA signal using a FDP for recommending best suited features. For GSR data the tool, 16 features were selected as most significant features. Similarly, for the method and system disclosed herein, all 84 features (21 features per channel for 4 channels) into the tool and it selected 30 features as the most significant ones. Out of these 30 features, 15 features corresponds to left and right hand signals. Remaining 15 features corresponds to leg signals. Corresponding classification performance is presented in Table 2.

TABLE 2

Comparison of Classification metrics
based on feature selection methods

| Feature Selection Method and Classifier | Sensor | No. Of Selected Features | f-score | Sensitivity | Specificity |
|---|---|---|---|---|---|
| FDP: 5-fold Cross Validation on Ensemble AdaBoost | GSR | 16 | 0.77 | 0.77 | 0.76 |
| | EDA | 30 | 0.89 | 0.9 | 0.89 |
| MIC: 10-fold Cross Validation on Random forest | GSR | 15 | 0.72 | 0.74 | 0.73 |
| | EDA | 25 | 0.85 | 0.87 | 0.86 |
| FDP: 10-fold Cross Validation on Random Forest | EDA| | 30 | 0.86 | 0.86 | 0.86 |
| FDP ∩ MIC: 10-fold Cross Validation on Random Forest | EDA | 15 | 0.85 | 0.86 | 0.86 |
| MIC: 10-fold Cross Validation on Random Forest | GSR and EDA | 40 | 0.89 | 0.90 | 0.89 |

It is to be noted that FDP gives classification performance on 5-fold cross-validation and the recommended classifier is ensemble AdaBoost. Also, Maximal information coefficient (MIC) based approach is tried for selecting most significant features. The results are presented in Table 2. For EDA, MIC based approach recommended 25 features giving an average classification accuracy of 86.5% with an f-score of 0.86. It is observed that, out of these 25 features, 16 features corresponds to leg signals and remaining 9 features corresponds to hand signals. For GSR, MIC recommends 15 features giving an average accuracy of 73.4%. Here random forest classifier is used, and classification performances are calculated using 10-fold cross validation. Next, the FDP recommended features were used and to perform 10-fold cross-validation using random forest classifier. Resultant average accuracy obtained is 86.6%. Next, attempt was made to derive a common set of features from FDP recommended features and MIC recommended features. It was observed that there are 15 features which are common to both the feature sets. Classification performance was derived using these common features only and obtained a classification accuracy of 86.1% using random forest classifier on 10 fold cross-validation as shown in Table 2. It was observed that classification performances are consistent across classifiers and feature sets selected by both FDP and MIC. Finally, we tried to merge GSR and EDA features. Average classification accuracy obtained with this merged set is 89.4% with an f-score of 0.89. Thus, the system and method disclosed herein can provide more accurate endosomatic EDA based approach for classification of low and high cognitive load.

Thus, the method and system disclosed herein utilizes endosomatic approach for assessment of cognitive load. Results suggest that bio-potential deviation signals vary significantly with different levels of cognitive load. It is observed that endosomatic EDA approach disclosed herein gives better classification accuracy compared to GSR signal. Statistical and frequency domain features of EDA signals gives a maximum classification accuracy of 83% (with specificity and sensitivity of 0.85 and 0.81) using 10 fold cross-validation approach. These performances are consistent even if FDP selected features or optimum set of features selected using FDP and MIC are used in random forest classifier for 10-fold cross validation. In all the above approaches, classification performance of EDA is better than GSR. Finally, by combining most significant GSR and EDA features, we obtained a classification accuracy of 89% using random forest classifier. Thus, it can be concluded that the endosomatic EDA signal in accordance with the system and method disclosed herein can alone be used to successfully differentiate between low and high cognitive load conditions and the results are consistent across various classifiers and feature selection algorithms. Assessment of cognitive load from endosomatic EDA signals have hardly been attempted before. Further, even though the cognitive task used herein refers to mental addition task, the method and system disclosed herein can be used for analysis of other cognitive tasks as well as for mental conditions like stress, anxiety etc. It was also observed that in exosomatic measurements, the external current applied changes the internal steady state equilibrium of our body, thereby changing the bio-potentials. The endosomatic approach for measuring cognitive load can be used in various applications like student assessment, cognitive assessment, mental health screening etc.

The written description describes the subject matter herein to enable any person skilled in the art to make and use the embodiments. The scope of the subject matter embodiments is defined herein and may include other modifications that occur to those skilled in the art. Such other modifications are intended to be within the scope of the present disclosure if they have similar elements that do not differ from the literal language of the present disclosure or if they include equivalent elements with insubstantial differences from the literal language of the embodiments described herein.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for assessment of cognitive load from bio-potentials, comprising:
   acquiring, via a multichannel wearable endosomatic device by one or more hardware processors, a plurality of bio-potential signals, wherein
   the plurality of bio-potential signals provides a task specific data of a subject performing a cognitive task,
   the cognitive task including one of a high load task or a low load task, and
   the plurality of bio-potential signals is time stamped;
   extracting, by the one or more hardware processors, baseline data and task data based on time stamps associated with each of the plurality of bio-potential signals, wherein
   the baseline data corresponds to segment of each of the plurality of bio-potential signals when the subject experiences a nil cognitive load during the cognitive task being performed, and
   the task data corresponds to segment of each of the plurality of bio-potential signals when the subject experiences an active cognitive load during the cognitive task being performed;
   deriving, by the one or more hardware processors, a plurality of deviation signals from the plurality bio-potential signals by:
   computing a mean of each of baseline data and the task data; and
   subtracting the computed mean from each of the baseline data and the task data;
   extracting, by the one or more hardware processors, a plurality of features from the plurality of deviation signals, wherein the plurality of features comprises a statistical set of features and a spectral set of features, wherein the spectral set of features comprises a mean frequency, a power at the mean frequency, a total power, a mean power, a median frequency, a power at median frequency, a peak frequency, a peak power, a signal band-power, a first moment, a second moment, and a third moment;
   determining, by the one or more hardware processors, an optimum set of features from the plurality of features wherein the determined set of features best differentiates between the high load task or the low load task; and
   training, by the one or more hardware processors, a classifier for classifying the cognitive task into one of the high load task or the low load task using the determined set of features, wherein the determined set of features is labeled as corresponding to the high load task or the low load task.

2. The processor implemented method of claim 1, wherein the method comprises utilizing the trained classifier to classify the cognitive task performed by the subject in real time into the high load task and the low load task.

3. The processor implemented method of claim 1, wherein the statistical set of features comprises:
   a mean, median, a standard deviation, skewness, kurtosis, minimum levels and maximum levels of the plurality of bio-potential signals using the task data; and
   normalized kurtosis and normalized variance values with respect to the baseline data and the task data.

4. A system for assessment of cognitive load from bio-potentials, comprising:
   a memory storing instructions;
   one or more Input/Output (I/O) interfaces; and
   one or more hardware processors coupled to the memory via the one or more I/O interfaces, wherein the one or more hardware processors are configured by the instructions to:
   acquire via a multichannel wearable endosomatic device, a plurality of bio-potential signals, wherein
      the plurality of bio-potential signals provides a task specific data of a subject performing a cognitive task, and
      the cognitive task including one or a high load task or a low load task, and
      the plurality of bio-potential signals is time stamped;
   extract baseline data and task data based on time stamps associated with each of the plurality of bio-potential signals, by the one or more hardware processors, wherein
      the baseline data corresponds to segment of each of the plurality of bio-potential signals when the subject experiences a nil cognitive load during the cognitive task being performed, and
      the task data corresponds to segment of each of the plurality of bio-potential signals when the subject experiences an active cognitive load during the cognitive task being performed;
   derive a plurality of deviation signals from the plurality bio-potential signals by:
      computing mean of each of baseline data and the task data; and
      subtracting the computed mean from each of the baseline data and the task data;
   extract a plurality of features from the plurality of deviation signals, wherein the plurality of features comprising a statistical set of features and a spectral set of features, wherein the spectral set of features comprises a mean frequency, a power at the mean frequency, a total power, a mean power, a median frequency, a power at median frequency, a peak frequency, a peak power, a signal band-power, a first moment, a second moment, and a third moment;
   determine an optimum set of features from the plurality of features wherein the determined set of features best differentiates between the high load task or the low load task; and
   train a classifier for classifying the cognitive task into one of the high load task and the low load task using the determined set of features wherein the determined set of features is labeled as corresponding to the high load task or the low load task.

5. The system of claim 4, wherein the one or more hardware processors are further configured to utilize the trained classifier to classify the cognitive task performed by the subject in real time into the high load task and the low load task.

6. The system of claim 4, wherein the set of statistical features comprises:
   mean, median, standard deviation, skewness, kurtosis, minimum levels and maximum levels of the plurality of bio-potential signals using the task data; and
   normalized kurtosis and normalized variance values with respect to the baseline data and the task data.

7. One or more non-transitory machine-readable information storage mediums comprising one or more instructions, which when executed by one or more hardware processors causes the one or more hardware processors to perform the steps of:
   acquiring, via a multichannel wearable endosomatic device, a plurality of bio-potential signals, wherein
      the plurality of bio-potential signals provides a task specific data of a subject performing a cognitive task,
      the cognitive task including one of a high load task or a low load task, and
      the plurality of bio-potential signals is time stamped;
   extracting baseline data and task data based on time stamps associated with each of the plurality of bio-potential signals, wherein
      the baseline data corresponds to segment of each of the plurality of bio-potential signals when the subject experiences a nil cognitive load during the cognitive task being performed, and
      the task data corresponds to segment of each of the plurality of bio-potential signals when the subject experiences an active cognitive load during the cognitive task being performed;
   deriving a plurality of deviation signals from the plurality bio-potential signals by:
      computing a mean of each of the baseline data and the task data; and
      subtracting the computed mean from each of the baseline data and the task data;
   extracting a plurality of features from the plurality of deviation signals, wherein the plurality of features comprises a statistical set of features and a spectral set of features, wherein the spectral set of features comprises a mean frequency, a power at the mean frequency, a total power, a mean power, a median frequency, a power at median frequency, a peak frequency, a peak power, a signal band-power, a first moment, a second moment, and a third moment;
   determining an optimum set of features from the plurality of features wherein the determined set of features best differentiates between the high load task or the low load task; and
   training a classifier for classifying the cognitive task into one of the high load task and the low load task using the determined set of features wherein the determined set of features is labeled as corresponding to the high load task.

8. The non-transitory machine-readable information storage mediums as claimed in claim 7, wherein the one or more hardware processors are further configured to perform the steps of utilizing the trained classifier to classify the cognitive task performed by the subject in real time into the high load task and the low load task.

* * * * *